US00PP36835P3

(12) United States Plant Patent
Olesen

(10) Patent No.: US PP36,835 P3
(45) Date of Patent: Jul. 22, 2025

(54) ROSE PLANT NAMED 'Poulvic002'

(50) Latin Name: *Rosa hybrida*
Varietal Denomination: Poulvic002

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,183

(22) Filed: Sep. 5, 2024

(65) Prior Publication Data

US 2025/0120327 P1 Apr. 10, 2025

(30) Foreign Application Priority Data

Sep. 22, 2023 (QZ) ..... PBR 20231986

(51) Int. Cl.
*A01H 5/02* (2018.01)
*A01H 6/74* (2018.01)

(52) U.S. Cl.
USPC ..... Plt./119
CPC ..... *A01H 6/749* (2018.05)

(58) Field of Classification Search
USPC ..... Plt./101, 116, 119
See application file for complete search history.

*Primary Examiner* — Karen M Redden

(57) ABSTRACT

A new garden rose plant of the Miniature class which has abundant, orange blend flowers and attractive foliage. This new and distinct variety has shown to be uniform and stable in the resulting generations from asexual propagation.

2 Drawing Sheets

Botanical designation: *Rosa hybrida.*
Variety denomination: 'Poulvic002'.

This application claims priority to Plant Breeder's Rights Application Number 2023/1986, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulvic002', originated as a single seedling from the stated cross.

The new variety may be distinguished from its male pollen parent and female seed parent primarily by the following characteristics. The male pollen parent plant has apricot flowers while the new variety has orange blend flowers. The female seed parent plant has pink blend flowers while the new variety has orange blend flowers.

The objective of the hybridization of this rose variety was to create a new and distinct variety with unique qualities, such as:

1. Uniform and abundant orange blend flowers;
2. Vigorous, but compact growth when propagated on its own roots;
3. Exceptional disease resistance.

This combination of qualities is not present in previously available commercial cultivars of this type, known to the inventor, and distinguish 'Poulvic002' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulvic002' was selected in the spring of (selection year) by the inventor as a single plant from the progeny of the aforementioned hybridization.

Asexual reproduction of 'Poulvic002' by rooted cuttings was first done by Mogens N. Olesen in the nursery in Fredensborg, Denmark in July, (selection year). This initial and other subsequent asexual propagations conducted in controlled environments have demonstrated that the characteristics of 'Poulvic002' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulvic002'.

Specifically illustrated in FIG. 1 of the drawings are open flowers, petals detached revealing reproductive flower parts, sepals detached showing receptacle.

Figure 1:
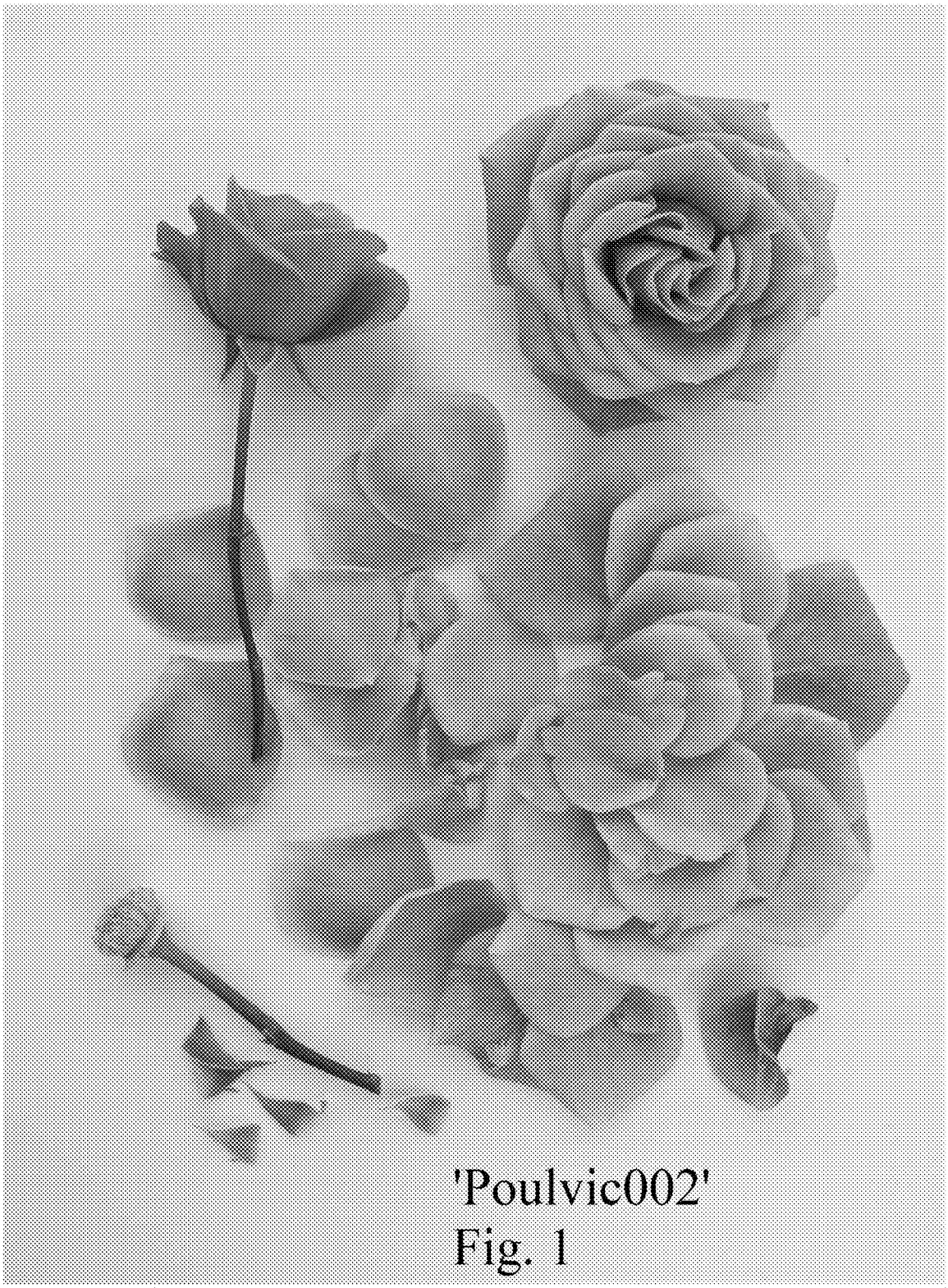
Figure 2:
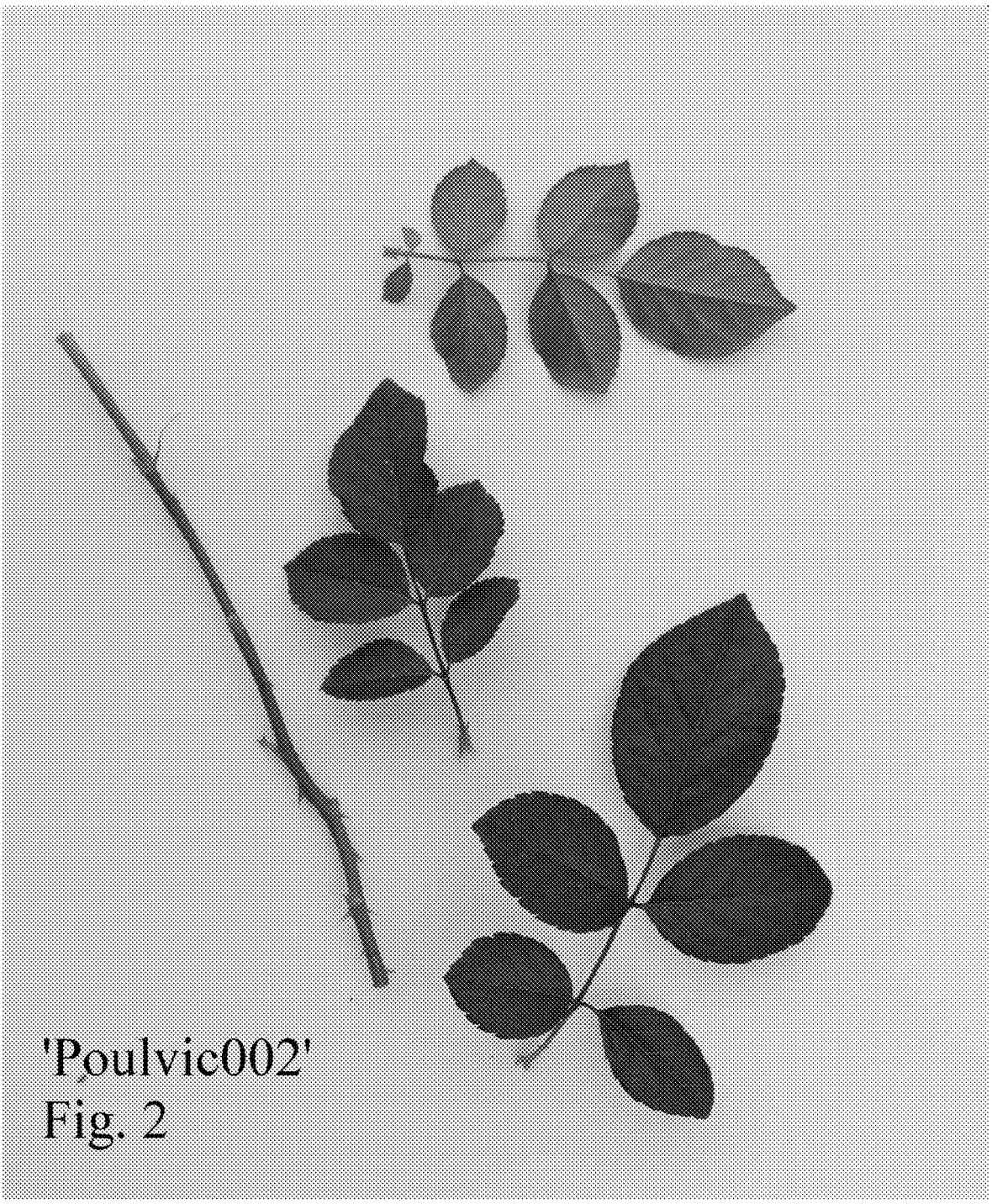

Specifically illustrated in FIG. 2 of the drawings are mature and juvenile leaves, and a bare stem exhibiting prickles. Plants shown are 5 months old.

DETAILED DESCRIPTION OF THE VARIETY

The following is a description of 'Poulvic002',as observed in its growth in a glass house nursery located in Odense Denmark. Observed plants are 5 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpal085', U.S. Plant Pat. No. 32,946 are compared to 'Poulvic002' in Chart 1.

CHART 1

| | 'Poulvic002' | 'Poulpal085' |
|---|---|---|
| Petal Count | 43 | 38 |
| Flower Diameter | 85 mm | 70 mm |
| General Tonality of Flower Color | Yellow-Orange Group 23C with other intonations of Red Group 51C | Orange Group 28C and Red Group 38A |

FLOWER AND FLOWER BUD

Blooming habit: Continuous.

Flower bud:

*Size.*—Upon opening, 18 mm in length from base of receptacle to end of bud. Bud diameter is 12 mm.

*Bud form.*—Ovoid.

*Sepal inner surface.*—Color: Yellow-Green Group 145C. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—About 21 mm long, 9 mm wide.

*Receptacle.*—Texture: Smooth. Size: 5 mm in height, 10 mm wide. Color: Yellow-Green Group 144A. Shape: Funnel.

*Pedicel.*—Surface: Smooth. Length: 32 mm. Diameter: 3 mm on average. Color: Yellow-Green Group 144A. Strength: Strong.

Flower bud development: Flower buds are borne single.

Flower bloom:

*Fragrance.*—Moderate floral scent.

*Duration.*—The blooms have a duration on the plant of approximately 21 days. Petals fall cleanly away from plant after flowers have fully matured.

*Size.*—Flower diameter is 85 mm when open. Flower depth is 33 mm.

*Flower shape.*—Slightly high centered, double, with a high pointed center which is tightly closed.

*Shape of flower, side view.*—The upper portion is slightly convex. The lower portion is flat.

Petalage: Under normal conditions, flowers have about 43 petals.

General tonality of flower: Open flowers are Yellow-Orange Group 23C with other intonations of Red Group 51C.

Petal color:

*Upon opening, outer petals.*—Upper surface: Orange Group 28B shaded with Red Group 41B. At the basal zone Yellow-Orange Group 14B. Lower surface: Orange-Red Group 32B, with streaking of Red Group 47C. At the basal zone, Yellow Group 5B.

*Upon opening, inner petals.*—Upper surface: Yellow-Orange Group 20A shaded with Orange-Red Group 33B. Lower surface: Yellow-Orange Group 22B shaded with Red Group 44C.

*After opening, outer petals.*—Upper surface: Red Group 55A. Marginal intonations of Orange Group 29A. At the basal zone Yellow Group 13B. Lower surface: Orange Group 29A with strong intonations of Red Group 54A. Basal zone Yellow Group 9B.

*After opening, inner petals.*—Upper surface: Yellow-Orange Group 22B with shades of Orange Group 29B. Basal zone Yellow Group 13B. Lower surface: Orange Group 24B with shades of Orange-Red Group 32C. At the basal zone Yellow Group 13B.

Petals:

*Petal reflex.*—Somewhat reflexed.

*Margin.*—Entire and uniform. Moderate undulations.

*Shape.*—Broad and elliptic. Apex shape: Rounded. Base shape: Acute.

*Size.*—About 44 mm (l)×46 mm (w).

*Texture.*—Smooth.

*Thickness.*—Average.

Petaloids:

*Size.*—25 mm (l) by 11 mm (w).

*Quantity.*—About 6.

*Shape.*—Nearly round with an obtuse base and rounded apices. Large cleft. Strong undulations of margin.

*Color.*—Underside is Orange Group 24C shaded with Orange Group 29B. Upper side Orange Group 24C shaded with Orange-Red Group 34C. Yellow Group 13A at the basal zone of both sides of petaloids.

Reproductive flower parts:

*Pollen.*—None observed.

*Anthers.*—Size: 2.5 mm in length. Color: Yellow Group 11B. Quantity: 65 on average.

*Filaments.*—Color: Yellow Group 8A. Length: 5 mm.

*Pistils.*—Length: 9 mm. Quantity: 45 on average.

*Stigmas.*—Color: Greyed-Yellow Group 162C.

*Styles.*—Color: Greyed-Yellow Group 162C with intonations of Red-Purple Group 58C.

*Location of stigmas.*—Superior in location relative to the length of the filaments and the height of the anthers.

*Hips.*—None Observed.

PLANT

Plant growth: Upright. Plants are about 37 cm in height, and 40 cm wide.

Stems:

*Color of juvenile growth.*—Yellow-Green Group 144B.

*Color of mature growth.*—Yellow-Green Group 146A.

*Length.*—Canes are about 21 cm from the base of the plant to the flowering portion.

*Diameter.*—About 4 mm.

*Internodes.*—On mature canes about 25 mm between nodes.

*Surface texture.*—Young wood: Smooth. Older wood: Smooth.

Long prickles:

*Incidence.*—13 prickles per 10 cm of stem.

*Size.*—Average length of prickles on mature stems is 5 mm.

*Shape.*—Upper portion is linear. Lower portion is concave.

*Color.*—Juvenile prickles: Mature prickles: Greyed-Purple Group 183C.

Plant foliage:

*Compound leaf.*—135 mm (l)×97 (w).

*Quantity*.—About 3, sometimes 4 leaves per 10 cm of stem on average.

*Leaf bearing angle to the stem.*—45 degrees.

*Color of juvenile foilage*.—Upper side: Yellow-Green Group 147A with intonations of Greyed-Purple Group 183A at margins. Lower side: Yellow-Green Group 147C with intonations of Greyed-Purple Group 183B shaded.

*Color of mature foliage*.—Upper side: Yellow-Green Group 147A. Lower side: Yellow-Green Group 147B.

Plant leaves and leaflets:

*Stipules*.—Size: 9 mm long, 2 mm wide. Quantity: 2 per compound leaf. Shape: Linear, slightly broad based with outward extending apices. Margins: Finely serrated. Color: Yellow-Green Group 144A.

*Petiole*.—Length: 23 mm. Diameter: 1.5 mm. Upper surface color: Yellow-Green Group 146A with intonations of Greyed-Purple Group 183A. Lower surface color:

*Rachis*.—Length: About 43 mm. Upper surface color: Yellow-Green Group 146A with intonations of Greyed-Purple Group 183A. Lower Surface color: Yellow-Green Group 144A.

*Leaflet*.—Quantity: Normally 5, occasionally 7 leaflets. Margins: Serrated. Size: Terminal leaflets are about 66 mm long, 39 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulvic002' substantially as described and illustrated herein.

* * * * *

'Poulvic002'

'Poulvic002'